(12) United States Patent
Holtwick et al.

(10) Patent No.: US 10,016,562 B2
(45) Date of Patent: Jul. 10, 2018

(54) MEDICAMENT GUIDING ASSEMBLY FOR A DRUG DELIVERY DEVICE

(71) Applicant: Sanofi-Aventis Deutschland GmbH, Frankfurt am Main (DE)

(72) Inventors: Marc Holtwick, Frankfurt am Main (DE); Martin Haupt, Vienna (AT)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 341 days.

(21) Appl. No.: 14/356,878

(22) PCT Filed: Nov. 15, 2012

(86) PCT No.: PCT/EP2012/072788
§ 371 (c)(1),
(2) Date: May 7, 2014

(87) PCT Pub. No.: WO2013/072439
PCT Pub. Date: May 23, 2013

(65) Prior Publication Data
US 2014/0364811 A1    Dec. 11, 2014

(30) Foreign Application Priority Data
Nov. 16, 2011    (EP) ..................................... 11189280

(51) Int. Cl.
*A61M 5/20* (2006.01)
*B29C 65/56* (2006.01)
(Continued)

(52) U.S. Cl.
CPC ............. *A61M 5/20* (2013.01); *B29C 65/148* (2013.01); *B29C 65/1435* (2013.01);
(Continued)

(58) Field of Classification Search
CPC ................ A61M 5/20; A61M 2207/00; A61M 2005/1787; A61M 5/19; B29C 66/73365;
(Continued)

(56) References Cited

U.S. PATENT DOCUMENTS 4,105,162 A    8/1978    Drori
5,725,363 A *  3/1998    Bustgens .............. F04B 43/043
                                                                417/207
(Continued)

FOREIGN PATENT DOCUMENTS

CN          1275884       12/2000
DE          4402119 A1    7/1995
(Continued)

OTHER PUBLICATIONS

English Translation of Abstract of Japanese Patent Application No. 2011-148293 dated Dec. 13, 2016.
(Continued)

*Primary Examiner* — Amber Stiles
(74) *Attorney, Agent, or Firm* — McCarter & English, LLP (57) ABSTRACT

The present invention relates to method of manufacturing a fluid guiding assembly for a drug delivery device and to a respective fluid guiding assembly. Said method comprising the steps of: providing a first member having at least one recess in a first surface portion, at least partially filling the recess with a joining component at least partially protruding from the first surface portion of the first member, arranging a second member having a second surface portion adjacent to the first member such that first and second surface portions thereof face towards each other to form an interface area between the first and the second members, wherein the joining component comprises a material different to the material of the first and/or second member wherein at least (Continued)

one channel structure extending along the interface area is formed by at least one deepening of the first member and/or of the second member, selectively providing thermal energy to the joining component to bond together first and second members.

20 Claims, 3 Drawing Sheets (51) Int. Cl.
```
A61M 5/24      (2006.01)
B29C 65/00     (2006.01)
B29L 31/00     (2006.01)
B29C 65/14     (2006.01)
B29C 65/16     (2006.01)
A61M 5/19      (2006.01)
A61M 5/178     (2006.01)
```
(52) U.S. Cl.
CPC ........ B29C 65/1483 (2013.01); B29C 65/168 (2013.01); B29C 65/1635 (2013.01); B29C 65/1683 (2013.01); B29C 65/565 (2013.01); B29C 66/1122 (2013.01); B29C 66/53461 (2013.01); B29C 66/73365 (2013.01); *A61M 5/19* (2013.01); *A61M 5/24* (2013.01); *A61M 2005/1787* (2013.01); *A61M 2207/00* (2013.01); *B29C 65/1406* (2013.01); *B29C 65/1409* (2013.01); *B29C 65/1416* (2013.01); *B29C 65/1422* (2013.01); *B29C 65/1606* (2013.01); *B29C 65/1609* (2013.01); *B29C 65/1616* (2013.01); *B29C 65/1622* (2013.01); *B29C 66/71* (2013.01); *B29C 66/712* (2013.01); *B29C 66/7392* (2013.01); *B29C 66/73921* (2013.01); *B29C 66/8322* (2013.01); *B29K 2995/0027* (2013.01); *B29K 2995/0056* (2013.01); *B29L 2031/753* (2013.01); *Y10T 29/4998* (2015.01)

(58) Field of Classification Search
CPC .............. B29C 65/1683; B29C 65/148; B29C 65/1635; B29C 65/565; B29C 65/168; B29C 65/1483; B29C 66/53461; B29C 65/1435; B29C 2995/0027; B29C 66/8322; B29C 65/1422; B29C 65/1606; B29C 66/73921; B29C 65/1409; B29C 65/1616; B29C 65/1406; B29C 65/1622; B29C 65/1609; B29K 2995/0027; B29K 2995/0056; Y10T 29/4998; B29L 2031/753

See application file for complete search history.

(56) References Cited

U.S. PATENT DOCUMENTS

| | | | |
|---|---|---|---|
| 6,283,730 B1* | 9/2001 | Sasaki | F04B 43/043 |
| | | | 417/413.3 |
| 9,511,191 B2* | 12/2016 | Holtwick | B29C 45/1671 |
| 2004/0026023 A1* | 2/2004 | DeMeter | B23Q 3/084 |
| | | | 156/247 |
| 2005/0074340 A1* | 4/2005 | Xu | F04B 19/006 |
| | | | 417/395 |
| 2005/0277882 A1 | 12/2005 | Kriesel | |
| 2010/0280461 A1* | 11/2010 | Forstreuter | A61M 5/31515 |
| | | | 604/228 |
| 2010/0318063 A1 | 12/2010 | Soll | |
| 2011/0243813 A1 | 10/2011 | Jackinsky et al. | |
| 2014/0316341 A1* | 10/2014 | Holtwick | A61M 5/31 |
| | | | 604/187 |

FOREIGN PATENT DOCUMENTS

| | | | |
|---|---|---|---|
| EP | 1002843 A2 | | 5/2000 |
| JP | 2007276172 A | * | 10/2007 |
| JP | 2011148293 A | | 8/2011 |
| WO | 99/18771 | | 4/1999 |
| WO | 2004092048 A1 | | 10/2004 |
| WO | 2005/088710 | | 9/2005 |
| WO | 2009023547 A2 | | 2/2009 |

OTHER PUBLICATIONS

Webb D.P., et al., "Packaging of Microfluidic Devices for Fluid Interconnection Using Thermoplastics," Journal of Microelectromechanical Systems, IEE Service Center, US, vol. 18, No. 2, Apr. 1, 2009, pp. 354-362.

* cited by examiner

MEDICAMENT GUIDING ASSEMBLY FOR A DRUG DELIVERY DEVICE

CROSS REFERENCE TO RELATED APPLICATIONS

The present application is a U.S. National Phase Application pursuant to 35 U.S.C. § 371 of International Application No. PCT/EP2012/072788 filed Nov. 12, 2012, which claims priority to European Patent Application No. 11189280.8 filed Nov. 16, 2011. The entire disclosure contents of these applications are herewith incorporated by reference into the present application.

FIELD OF INVENTION

The present invention relates to a fluid guiding assembly for a drug delivery device providing at least one fluid channel adapted to guide a fluid, e.g. a medicament. The invention further relates to a method of a manufacturing such a fluid guiding assembly.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

For instance, such devices comprise a housing to receive a cartridge being at least partially filled with the medicament to be dispensed. The device further comprises a drive mechanism, typically having a displaceable piston rod to operably engage with a piston of the cartridge. By means of the drive mechanism and its piston rod, the piston of the cartridge can be displaced in a distal or dispensing direction and may therefore expel a pre-defined amount of the medicament via a piercing assembly which is to be releasably coupled with a distal or dispensing end of the housing of the drug delivery device.

Depending on the type of medicament and the way the medicament has to be prepared prior to be administered to a patient, particular drug delivery devices have to provide a medicament guiding structure, e.g. downstream of a cartridge but upstream of a dispensing end. Manufacturing of such fluid guiding structures or fluid guiding channels is somewhat crucial. Especially when the fluid guiding structure is made of plastic, in particular of thermoplastic material, a desirable miniaturization of fluid guiding structures or channel structures is difficult to achieve. For instance by way of injection molding processes complicated or multiply wound hollow channel structures cannot be realized.

Especially with drug delivery devices and applications it would be of particular benefit to provide fluid guiding channels with a comparatively small cross section in order to minimize a dead volume of the fluid guiding structure for not unnecessarily wasting precious or expensive medicaments or the like substances to be guided therethrough.

Moreover, fluid guiding plastic components should be substantially inert or highly compatible to the medicament or substance to be guided therewith. Hence, the range of plastic components suitable for medicament guiding purposes is rather limited.

In general, small sized channel structures can be manufactured by providing a member featuring a channel-forming groove or recess extending across a surface portion. By covering the surface portion with a cover part and by bonding cover part and said member together, a closed fluid-guiding channel structure can be provided in principle. Bonding of the member and the cover part may be provided by way of laser welding or ultrasonic welding as well as by making use of adhesives. Such mutual bonding of member and cover part involves application of heat, which may eventually deteriorate the chemically inert properties of the respective plastic material.

Moreover, chemically inert plastic materials are rather unsuitable for e.g. laser welding due to insufficient light absorption properties. Enhancement of light absorption can in principle be attained by embedding light absorbing particles, such like soot particles, in the bulk of such plastic materials. However, this may further deteriorate the purity of the plastic material and pre-defined as well as required chemically inert properties may no longer be met.

Also, when bonding the member and the cover part together by means of an adhesive, a portion of the adhesive may intrude into the channel structure, thereby enhancing a risk, that the medicament flowing therethrough gets contaminated.

SUMMARY

It is therefore an object of the present invention to provide a fluid guiding assembly for a drug delivery device which is easy to assemble and which provides a liquid-tight channel structure of pre-defined size and/or geometry without the necessity to directly apply thermal energy to channel forming members. The invention therefore aims to provide an improved method of manufacturing a fluid guiding assembly without deteriorating the plastic component the channel structure is made from. Said method of manufacturing should be highly reproducible and should provide a long lasting liquid-tight fluid guiding channel structure in plastic-based members or parts of a fluid guiding assembly.

In a first aspect, the invention provides a method of manufacturing a fluid guiding assembly for a drug delivery device. Here, in a first step a first member is provided having at least one recess in a first surface portion. In a second step, said recess is at least partially filled with a joining component, which comprises a material different to the material, the first member is made of.

Thereafter, a second member is arranged preferably on top of the first member to accommodate the joining component between first and second members, respectively. The second member has a second surface portion facing towards the first surface portion of the first member. The second member is to be arranged adjacent to the first member such that first and second surface portions thereof face towards each other to form an interface area between the first and second members.

At least one of first or second members comprises at least one channel structure extending along the interface area of first and second members. The channel structure is formed by at least one deepening or groove extending in the first or second surface portion, respectively. By way of the deepening, at least one closed channel structure extending along the interface area of first and second surface portions can be formed by bringing first and second members in a mutual abutment configuration.

After mutually arranging first and second members, with respect to each other, thermal energy is selectively provided to the joining component to bond together first and second members. The joining component is particularly adapted to melt in response of thermal energy application, which may take place e.g. by way of absorption of electromagnetic radiation within a pre-defined spectral range.

Initially and prior to apply thermal energy to the joining component, the joining component at least partially protrudes from the first surface of the first member. This way, first and second surface portions of first and second members can be kept at a certain distance with respect to each other prior to thermal energy application. Once the joining component is subject to melting in response of energy application, the first and second members can establish a mutual abutment configuration, for example when subject to a compressive force.

Consequently, and according to a further embodiment, thermal energy is provided into the joining component by way of absorbing electromagnetic radiation. Hence, the preassembled fluid guiding assembly, wherein first and second members as well as the joining component are loosely fitted, is exposed to electromagnetic radiation. Preferably it is exposed to substantially monochromatic radiation emitted by a laser. It is of particular benefit, when the radiation is precisely focused or spatially confined in the region in which the joining component extends.

The choice of the material of the joining component particularly matches with the absorption properties of the joining component. It is of further benefit, when at least one of first and second members, preferably when both, first and second members comprise a comparatively low absorption coefficient for the selected electromagnetic radiation.

It is of particular benefit, when according to another embodiment first and second members are pressed together during application of thermal energy to the joining component. This way, first and second members may be subject to an eventual compensative motion which may be beneficial for compensating eventual flatness tolerances of the mutually corresponding surface portions of first and second members, respectively. Moreover by making use of a number of pressure pieces adapted to apply compressive pressure to first and/or second members, a pressure distribution across first and/or second surfaces may become rather homogeneous. In effect, by way of a rather homogeneous pressure application the reliability and repeatability of a laser welding process can therefore be enhanced.

In a further embodiment, the second member comprises at least one recess in the second surface portion. This recess corresponds in size and position with the at least one recess of the first surface portion of the first member. When arranging first and second members in a mutual abutment configuration, the joining component provided in the recess of the first member may extend into the recess of the second member. The joining component extending from the first surface may therefore provide an assembly aid for bringing together first and second members in a well-defined mutual abutment configuration. By means of mutually corresponding recesses and by means of the joining component received therein, first and second members can be easily positioned, oriented and aligned with respect to each other.

Here, it is even conceivable, that the joining component either frictionally or positively engages with a correspondingly formed recess of the second member, thereby providing a well-defined pre-assembly of first and second members.

In a further preferred embodiment, the extension of the joining component in a direction parallel to the surface normal of first and/or second surface portions of first and second members, respectively, is substantially larger than the sum of the respective depths of mutually corresponding recesses of first and second members. Having the joining component pre-assembled in the at least one recess of the first member and arranging the second member to the first member in such a way, that its recess receives the protruding free end of the joining component, then first and second surface portions remain at a certain distance with respect to each other. It is only upon applying thermal energy to the joining component and by melting the joining component that first and second surface portions of first and second members may then get in direct mutual contact. Here, excess material of the joining component may either distribute in the mutually corresponding recesses of first and/or second members or may even spread and distribute in the interface area of first and second members.

According to a further embodiment, the recess of the second member is wider than the recess of the first member. This way, the joining component can for instance be frictionally engaged or can be otherwise secured in the recess of the first member. Given that the joining component comprises a continuous and elongated shape parallel to the surface normal of first and/or second surface portions, a lateral gap will form between the protruding portion of the joining component and the recess of the second member, when the second member is in a respective pre-assembly position. The respective width of the second members' recess allows to arrange the second member within a given tolerance ranges in lateral direction, i.e. parallel to the plane of first and/or second surface portion of first and second members. This way, a mutual relative arrangement and alignment in lateral direction can be provided prior to bond together first and second members.

In another embodiment, the recess of the second member is wider in lateral direction compared to a lateral extension of the joining component. In this way and as already described above, receiving the joining component in the recess of the second member allows for a relative mutual alignment of first and second members in lateral direction.

Alternatively, it is also conceivable that the joining component is pre-assembled in the at least one recess of the second member in such a way, that the joining component enters the corresponding recess of the first member when bringing together first and second members in a pre-assembly configuration. It is of particular benefit, when the recess of first and/or second member, which is adapted to receive the joining component during the mutual assembly of first and second member, comprises a lateral width or diameter being larger than a corresponding width, cross section or diameter of the joining component to be received therein.

It is even conceivable, that first and second members comprise at least two separated recesses, wherein at least one recess of both, first and second members is initially at least partially filled with a joining component protruding from the respective member to enter a corresponding recess of the other member, respectively.

In a further embodiment, excess material of the joining component extends into and fills lateral gaps between the joining component and the recess of the second member when the joining component is melted. Depending on the particular configuration of the joining component and mutually corresponding recesses of first and second members, it is also conceivable, that excess material of the joining component fills a lateral gap between the joining component and a corresponding recess of the first member.

Generally, by having the joining component at least partially protruding from the first surface of the first member, a pre-assembly configuration with the sealing second member can be attained, wherein a vertical gap between first and second surfaces of respective first and second members can be attained. In this configuration, both members are in direct contact with the joining component. Applying thermal energy to the joining component may then lead to a melting of said joining component, wherein a contact with first and second members can be attained.

Moreover, under the effect of gravity or pressure, the melting or melted joining component may homogeneously distribute in the at least one recess of the first member or in mutually corresponding and substantially overlapping recesses of first and second members, respectively. The thermally induced melting of the joining component also leads to a reduction of the vertical gap between first and second surfaces. Preferably, said gap is completely closed during the electromagnetically induced melting of the joining component. Hence, the size of a vertical gap between first and second surface portions of first and second members may be directly indicative of the quality and the progress of the melting of the joining component and the respective bonding of first and second members.

Hence, in a further preferred embodiment, the vertical gap size between first and second surface portions can be used to control energy deposition into the joining component. Consequently, thermal energy is provided to the joining component, preferably by absorption of laser radiation, until first and second surfaces of first and second members mutually abut in direct mechanical contact, thereby providing an effective sealing of the channel structure extending along the interface area of first and second members.

In another aspect a fluid guiding assembly for a drug delivery device is provided being assembled by the method as described above. The fluid guiding assembly comprises a first member having at least one recess in a first surface portion. The fluid guiding assembly further comprises a second member adjacently disposed to the first member. The second member has a second surface portion facing towards the first surface portion of the first member to form an interface area between first and second members, especially when getting in direct mutual contact. Consequently, first and second surfaces of first and second members face towards each other and may even get in direct contact or direct abutment with each other.

Additionally, the fluid guiding assembly comprises at least one channel structure extending along the interface area of first and second members. The channel structure is formed by at least one deepening or groove provided in the first member and/or in the second member.

In particular, the channel structure can be established by forming a groove in e.g. the first surface portion of the first member and by covering said groove by means of a substantially flat-shaped or correspondingly grooved or deepened second member being in abutment configuration with the first member. This way, a channel structure in the interface area of first and second members can be formed, wherein each of the mutually abutting surface portions of first and second member laterally enclose the channel structure.

Typically, first and second surface portions of first and second members may mutually complement to provide a channel structure extending along the interface area and being surrounded in lateral direction by the surface profiles of first and second mutually interconnected members.

Furthermore and in order to interconnect or to bond first and second members, the at least one recess provided in the first surface portion of the first member is at least partially filled with a joining component which comprises a material different to the material of the first and/or the second member. The joining component is preferably arranged in said recess in such a way that it gets in direct contact with the first member as well as with the second member arranged in mechanical contact with the joining component and/or with the first member. Preferably, the joining component completely fills the recess of the first member.

By making use of a particular joining component different to the material of first and/or second members, first and/or second members can be integrally joined or adhesively bonded without applying or depositing thermal energy thereto. It is the joining component sandwiched between first and second members and being particularly adapted for thermal energy application to firmly bond together first and second members. As a consequence, it is no longer required to directly apply thermal energy to the first and/or second member.

In effect, biocompatible or chemically inert plastic components, first and/or second members are preferably made of do not longer have to be modified for e.g. a thermal treatment based bonding procedure, such like laser welding. By providing a separate joining component between those members that form a channel structure therebetween a risk of deteriorating first and second members as well as a risk of mechanically deforming first and/or second members during e.g. a laser welding procedure can be minimized advantageously.

According to preferred embodiment, the joining component comprises a larger absorption coefficient for a pre-defined spectral range of electromagnetic radiation than the material of the first and/or second members. The joining component may be selected according to the spectral range of available sources of electromagnetic radiation. In particular, the joining component may be doped with a particular dye or with radiation absorbing particles that match with a pre-defined spectral range.

Generally, it is of particular benefit, that the recess and the joining component are spatially separated from the channel structure. Therefore, the joining component does not have to be of biocompatible or FDA-compliant type. In general, any suitable material or substance can be used as joining component which absorbs thermal energy in response to exposure to a selected spectral range of electromagnetic radiation. Moreover, the joining component should expose a melting and bonding effect when exposed to electromagnetic radiation of a pre-defined spectral range. In principle, there is no limitation regarding the choice of the joining component and a corresponding spectral range of electromagnetic radiation, as long as the joining component exhibits a substantial absorption coefficient regarding the electromagnetic radiation. However, for practical reason, the spectral range may be in the UV, within the visible spectrum and/or in the near or far infrared spectrum of electromagnetic radiation.

In a further preferred aspect, the first and/or the second members of the fluid guiding assembly are substantially transparent or non-absorbing regarding the pre-defined spectral range of electromagnetic radiation. This way, thermal energy can be selectively and precisely applied to the joining component sandwiched between first and second members. Since the first and/or second members are substantially transparent in the pre-defined spectral range of electromagnetic radiation, their degree of absorption is comparatively low. Consequently, even high intensive or highly focused electromagnetic radiation within the pre-defined spectral range may not induce a substantial heating of first and/or second members. First and second members featuring a liquid guiding channel structure for a liquid component in particular for a liquid medicament may therefore remain substantially unaffected by the electromagnetic radiation applied e.g. in a laser welding procedure.

In a preferred aspect the first and/or the second member comprise a plastic material and may be created by way of injection molding. This way, first and/or second members can be inherently provided with a recess or groove extending along a particular surface portion thereof to at least partially form the channel structure which is to be closed by bringing first and second member in direct abutment with respect to each other. The first member and/or the cover part preferably comprise a plastic material being substantially inert to substances to be led through the channel structure. The materials first member and cover member are made of should therefore be classified as biocompatible. Preferably the first member and/or the cover part comprise a plastic material being approved by the US Food and Drug Administration (FDA). Consequently, the plastic materials of choice meet the standards according to US government regulation (CFR) 21 and are classified as FDA compliant. Among FDA-compliant plastic materials first body part and/or cover part may comprise plastic materials such like Cyclo Olefin Polymers (COP).

In a further preferred aspect, the first and second members of the fluid guiding assembly are bonded together by means of selectively applying thermal energy to the joining component sandwiched between first and second members. Preferably, energy application is conducted by absorption of electromagnetic radiation of a pre-defined spectral range that matches with optical absorption properties of the joining component.

Preferably, energy application, hence exposure of electromagnetic radiation, is accompanied by pressing together first and second members. This way, the channel structure formed in the interface area of first and second members can be effectively sealed to provide fluid tightness.

In this context, it is of further benefit, when first and second surfaces of first and second members mutually abut in a direct mechanical contact configuration. This way, a firm interconnection of first and second members providing a liquid-tight seal for the channel structure disposed there between can be established.

In a further embodiment, the second member extends across the deepening of the first member to form a closed fluid guiding channel structure. In such examples, wherein the channel structure of the channel-forming deepening is exclusively present in the first member, the second member may serve as a cover to close the deepening and to form an enclosed channel structure. In other configurations, wherein the channel structure is complemented by two mutually corresponding deepenings or grooves of first and second members, it is also due to mutual abutment and direct mechanical contact of first and second surface portions that a sealed channel structure can be formed.

Moreover, the second member also extends across the recess of the first surface portion in order to get in direct mechanical contact with the joining component.

In a further preferred aspect, the at least one recess to receive or to accommodate the joining component is arranged outside the spatial extent of the deepening that serves to provide or which is intended to form the channel structure. This way, the area which is subject to thermal energy application can be kept away from the fluid guiding channel structure. In effect, the material of first and second members in direct vicinity of the channel structure can remain substantially unaffected of thermal energy application that takes place in a remote recessed portion of the first member.

In a further preferred embodiment, at least two recesses are arranged on opposite lateral sides of the deepening of the interface area. This way, an integral joining or an adhesive bonding between first and second members can be established at several locations across first and second surfaces in order to provide a substantially homogeneous bonding of first and second members.

Alternatively, a single or several recesses provided in the first member may enclose the cavity of the interface area. Hence, the deepening adapted to form the at least one fluid guiding channel structure can be encased or bordered by the recess which is adapted to receive the joining component. Here it is even conceivable that one or more recesses are provided in a rather concentric arrangement.

In a further preferred embodiment, it is not only the first member featuring a recess but also the second member that comprises at least one recess that corresponds or mates with the at least one recess of the first member. Such an embodiment is of particular use, when the joining component substantially protrudes from the surface portion of the first member. Preferably, the extension of the joining component in a direction along the surface normal of first and/or second surface portions is larger than the sum of the depths of mutually corresponding first and second recesses.

This way, first and second members when arranged on top of each other mutually abut via the joining component while a gap is formed between first and second surface portions of first and second members. For bonding together first and second members, thermal energy is to be provided to the joining component, which in response thereof starts to melt. It is of particular benefit, when the volume of the joining component substantially matches with the volume of mutually corresponding first and second recesses of first and second members.

Upon melting the joining component, the first and second members can be brought in direct mechanical contact with each other, wherein a mutual abutment can be supported by applying respective compression force or pressure to first and/or second members. By way of a melting-accompanied bringing together of first and second members, eventual irregularities of the flatness of first and/or second surfaces can be compensated, thereby enhancing the quality of the sealing.

In a further preferred aspect, the fluid guiding assembly is designed as a needle hub or as a cartridge hub of a drug delivery device, which for instance provides administering of a medicament by way of injection. The guiding assembly may be of particular use with drug delivery devices, wherein two or more medicaments provided in different cartridges have to be combined or mixed prior or during delivery to a patient. Such a guiding assembly has further application in circumstances, wherein different medicaments provided by different containers or cartridges are to be dispensed in a sequential manner through a common single dispensing outlet of the drug delivery device. Hence, the guiding assembly may be used as a 2-in-1 junction member or as a T-piece guiding member. Typically, such fluid guiding assembly is to be arranged downstream of a medicament containing the cartridge of a drug delivery device but upstream of a dispensing end, which may be in fluid connection with a replaceable injection needle or other fluid guiding structures.

According to a further independent aspect the invention also relates to a drug delivery device adapted to dispense a pre-defined amount of at least one medicament via an outlet. The drug delivery device, which may be designed as a hand-held injector or as a pen-type injector comprises a housing to receive at least one cartridge being at least partially filled with a medicament. Moreover, the device comprises a dispensing end via which a pre-defined amount of the medicament is to be dispensed. Furthermore, the drug delivery device comprises a fluid guiding assembly as described above being disposed in a fluid path between the cartridge or at least one of the cartridges and the dispensing end, so that the at least one channel structure provided by the fluid guiding assembly can provide a respective fluid guiding functionality.

In a further preferred aspect also a fluid guiding pre-assembly to form a fluid guiding assembly as described above is provided. The fluid guiding pre-assembly comprises at least a first member having at least one recess in a first surface portion and further comprises a joining component at least partially filling said recess and at least partially protruding from the first surface portion of the first member. The joining component comprises a material different to the material of the first member to selectively receive thermal energy for bonding together the first member with a second member.

Preferably and as already described above, the second member is to be arranged in close proximity to the first member in a configuration in which it gets in direct contact with the protruding portion of the joining component. By selectively applying thermal energy to the joining component in a final bonding procedure, the joining component starts to melt and thereby bonds together first and second member.

The first member and/or the second member to be bonded thereto further comprise a channel structure which extends along the interface area formed by at least one deepening of the first member and/or of the second member. By bonding first and second members by means of the joining component, the channel structure can be effectively sealed.

In a preferred aspect, the joining component is pre-assembled in the recess of the first member. For instance, the first member may comprise an injection molded plastic component and the joining component may be injection molded in the recess of the first member, thereby inseparably interconnecting the joining component with the first member.

In general, all features and embodiments as described and illustrated with respect to the fluid guiding assembly equally apply to the fluid guiding pre-assembly.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

```
H-(Lys)4-des Pro36, des Pro37 Exendin-
4(1-39)-NH2,

H-(Lys)5-des Pro36, des Pro37 Exendin-
4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-
4(1-39), des Pro36 [Trp(O2)25, Asp28] Exendin-
4(1-39), des Pro36 [Trp(O2)25, IsoAsp28] Exendin-
4(1-39), des Pro36 [Met(O)14 Trp(O2)25, Asp28]
Exendin-4(1-39),
``` des Pro36 [Met(O)14 Trp(O2)25, IsoAsp28]
Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp (O2)25,Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2), Asp28] Exendin-4(1-39)-(Lys)6-NH2, H-(Lys)6-des Pro36, Pro37, Pro38 [Trp(O2), Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+ or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically Acceptable Solvates are for Example Hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention. Moreover, all features and embodiments as described herein are to be understood to equally apply to the fluid guiding assembly, to the drug delivery device as well as to the method to manufacture the fluid guiding assembly. In particular, a mentioning of a component being configured or arranged to conduct a particular operation is also to be understood to disclose a respective method step and vice versa.

BRIEF DESCRIPTION OF THE DRAWINGS

In the following, preferred embodiments among a manifold of optional and equally conceivable ways to carry out the invention will be described by making reference to the drawings, in which.

DETAILED DESCRIPTION

In the sequence of FIGS. 1 to 5 a method of manufacturing or assembling of a fluid guiding assembly 10 is illustrated. Initially, a first member 12 is provided featuring an upward facing first surface portion 22 being intersected by a groove-like deepening 14 and by two recesses 16, 18. The deepening 14 as well as the recesses 16, 18 extend in the plane of the first surface portion 22.

Figure 1:
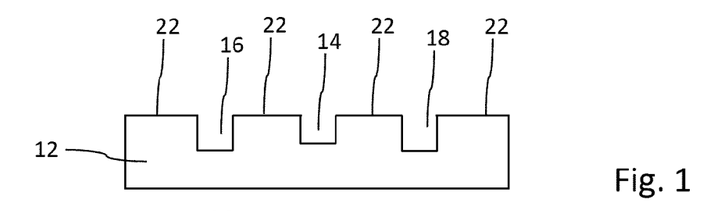
FIG. 1 shows a first member of the fluid guiding assembly in an initial configuration in a cross sectional side view.

The recesses 16, 18 can be designed separate from each other. However, the illustrated recesses 16, 18 may also be portions of a single recess circumfering or enclosing the deepening 14 in the plane of the first surface portion 22.

Any or at least one of the illustrated recesses or deepenings 14, 16, 18 can be separately introduced or crafted into the material of the first member 12. Alternatively, the first member 12 can be readily provided or manufactured by e.g.

an injection molding step to create the first member 12. The member 12 is preferably made of a thermoplastic material, preferably of a biocompatible or FDA-compliant plastic material.

Figure 2:
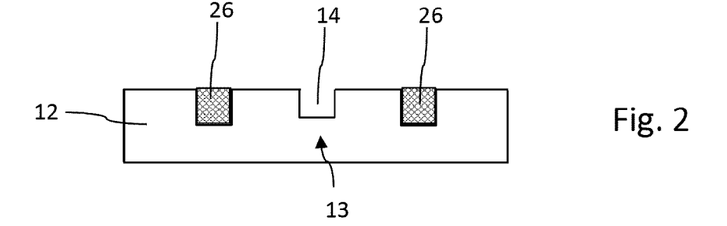
FIG. 2 shows the first member with joining components deposited in recesses.

As illustrated in FIG. 2, the recesses 16, 18 located sidewards with respect to the deepening 14 are at least partially filled with a joining component 26. The joining component 26 comprises a material composition different to the material of the first member 12. The joining components 26 or a single joining component 26 is shaped to fit into the recesses 16, 18 as illustrated in FIG. 2. The joining components 26 can be press-fitted or integrally formed and arranged in the recesses. It is also conceivable, that the joining components 26 and the first member 12 are injection molded, e.g. by way of a two- or multi-component injection molding process. Moreover, the joining components 26 may positively engage with the first member 12 and its recesses 16, 18, e.g. when featuring undercuttings and/or corresponding protrusions, of for instance dove-tail shape.

In particular, FIG. 2 illustrates a fluid guiding pre-assembly with the joining component 26 arranged in and protruding from recesses (16, 18) of the first member 12.

Figure 3:
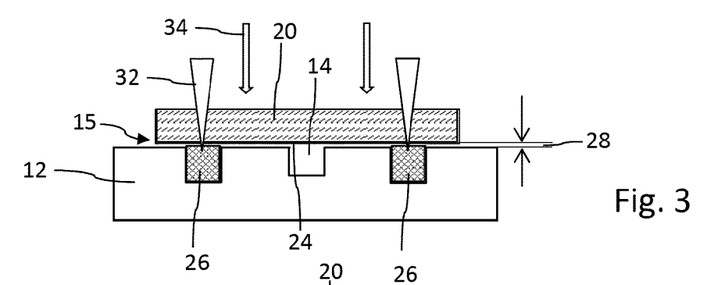
FIG. 3 is illustrative of a laser welding process to adhesively bond first and second members and FIG. 4 shows the fluid guiding assembly in a final assembly configuration.

Thereafter, a second member 20, illustrated as a substantially flat-shaped plate-like member is arranged on top of the first member 12. The second member 20 features a lower or downward facing second surface portion 24 facing towards the upper, first surface portion 22 of the first member 12.

As illustrated in FIG. 3, the joining component 26 at least slightly protrudes from the first surface portion 22. Hence, in the illustrated pre-assembly configuration, the second member 20 is disposed on top of the first member 12 and is supported in exclusive mechanical contact with the upward facing surface portion of the joining components 26 protruding from respective recesses 16, 18. This way, a small gap 28 between first member 12 and second member 20 is formed. When the fluid guiding assembly is preassembled as depicted in FIG. 3, the joining components 26 become subject to selective thermal energy application, e.g. by exposing high intensity and/or focus laser radiation 32 into the area of the joining component 26.

Since the material of the second member 20 and/or of the first member 12 features a comparatively small degree of absorption with regard to the laser radiation 32 of choice, a major portion of the radiation energy can be effectively and exclusively provided in or on the joining components 26. Hence, the optical absorption characteristics of the material the joining components 26 are made from is designed and/or is adapted to the selected spectral range of electromagnetic radiation 32.

Figure 4:
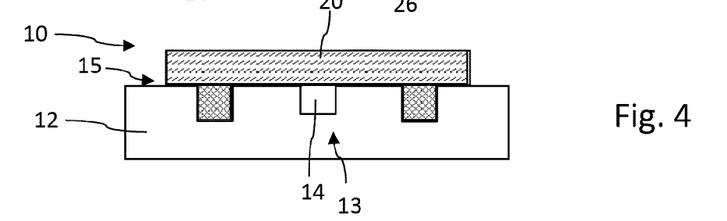

The U-shaped groove or deepening 14 provided in the upper first surface portion 22 of the first member 12 is covered and enclosed by the downward pointing second surface portion 24 of the second member 20. In the course of melting the joining component 26 also a compressive force 34 may be applied on top of the second member 20 so as to bring the surface portions 22, 24 of first and second members 12, 20 in a direct mutual and sealing abutment configuration as indicated in FIG. 4. Consequently, a closed and liquid-tight channel structure 13 can be formed in an interface area 15 between first and second members 12, 20.

As further indicated in FIG. 4, a liquid-tight seal can be provided between the deepening 14 and the adjacently positioned second surface portion 24. This way, a thermally induced bonding or integral joining of first and second members 12, 20 can be attained without providing thermal energy into said components, which may be sensitive to heating.

Figure 5:
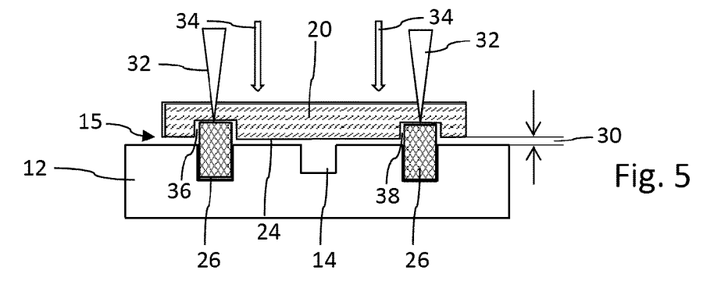
FIG. 5 is further indicative of a laser welding procedure with joining components protruding from the first surface of the first member and keeping first and second members in a spaced appart configuration.

FIG. 5 is indicative of a further embodiment wherein the second component 20 in contrast to the embodiment as depicted in the sequence by FIGS. 1 to 4 comprises recesses 36, 38 in the downward facing second surface portion 24. Size and position of the recesses 36, 38 corresponds with the size and the position of recesses 16, 18 provided in the first surface portion 22 of the first member 12. As further illustrated in FIG. 5, the joining components 26 extend in a direction parallel to the surface normal of first and/or second surface portions 22, 24. Vertical extension of joining components 26 is substantially larger than the sum of the respective depths of recesses 16 and 36 and/or of recesses 18, 38.

As further illustrated in FIG. 5, the recesses 36, 38 of the second component may be wider than the recesses 16, 18 of the first component or slightly wider than the lateral extension of the joining components 26. The joining components 26 which completely fill the recesses 16, 18 of the first component 12 may extend into the downward facing recesses 36, 38 of the second component 20 such that a lateral gap forms. Upon melting of the joining components 26, excess material of the joining components 26 may extend into and fill these lateral gaps.

In a pre-assembly configuration as indicated in FIG. 5, also a vertical gap 30 between first and second surface portions 22, 24 can be attained, which minimizes to zero once the joining component 26 becomes subject to thermal energy application and starts to melt.

Additionally, as illustrated in FIGS. 3 and 5, thermal energy application induced by e.g. electromagnetic radiation 32 can be accompanied by a compressive force 34 by way of which first and second members 12, 20 can be firmly pressed together. When first and second components 12, 20 are kept and a non-abutting distance 28, 30 from each other prior to application of thermal energy, the melting process of the joining component 26 can be accompanied at least by slight relative displacement of first and second members 12, 20, also parallel to the plane of first and second surface portions 22, 24, thereby compensating eventual flatness tolerances of first and/or second members 12, 20.

The embodiment according to FIG. 5 is also beneficial in terms that the focal spot or the focal level, where radiation 32 enters the joining component 26 can be slightly raised, e.g. at least by the size of the gap 30. Hence, the location, where thermal energy is provided or applied into the joining component 26 can be moved further away from the channel structure 13 thereby reducing thermal stress in direct or close vicinity of the channel structure 13. This may lead to an improved seal and to a better repeatability as well as reproducibility of the laser welding process.

Moreover it has to noted that the channel structure 13, can be formed in the interface area 15 by a multiplicity of different ways. Mutually corresponding or complementing recessed structures or grooves of first member 12 and/or second member 20 may be of rectangular, oval, circular shape. Also, a rather quadratic or rectangular channel structure may be formed by means of two mutually corresponding v-shaped grooves provided in the first member 12 and the second member 20, respectively In FIG. 6, a flowchart of the various steps to manufacture or to assembly a fluid guiding assembly 10 as shown in the sequence of FIGS. 1 to 5 is schematically illustrated. Hence, in a first step 100, a first member 12 is either supplied or provided or is manufactured, e.g. by way of injection molding. Thereafter, in step 102, the at least one recess 16, 18 extending in the first surface portion 22 of the first member 12 is at least partially filled with a joining component 26.

Figure 6:
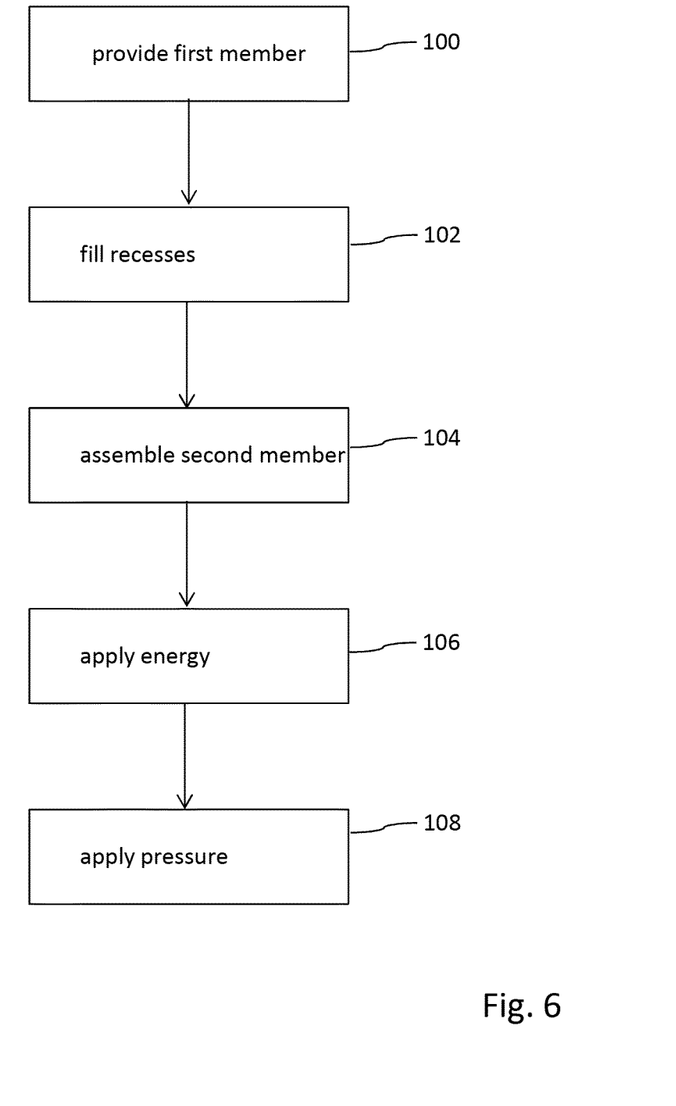
FIG. 6 shows a flowchart to conduct a method of assembly.

Subsequently, in step 104, a second component 20 is placed on top of the first component 12, wherein the second member 20 preferably gets in direct contact with the non-melted joining component 26. Thereafter, in step 106 and as shown in FIG. 3, thermal energy is provided in the joining component 26 leading to a melting of said component 26 and to the formation of an adhesive bond between the joining component 26 and adjacently arranged first and second members 12, 20 being in direct mechanical contact therewith.

The application of thermal energy is preferably accompanied or correlated with the application of a compressive force 34, preferably evenly distributed across the surface portions 22, 24 of first and second members 12, 20. This way, a precise and well-defined adhesive bonding or integral join between first and second members 12, 20, which may be made of the same plastic material can be established.

Figure 7:
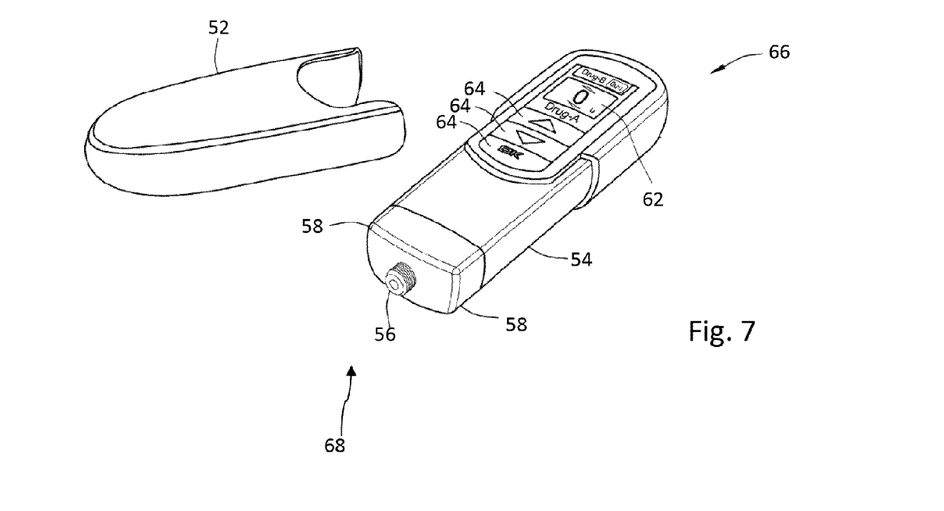
FIG. 7 is illustrative of a drug delivery device making use of the present fluid guiding assembly and FIG. 8 shows the drug delivery device according to FIG. 7 in a partially transparent view.
Figure 8:
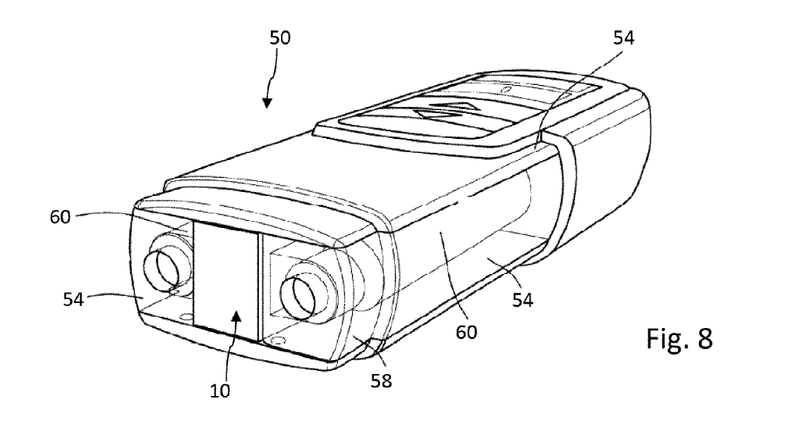

FIGS. 7 and 8 are finally indicative of a hand-held drug delivery 50 having a housing 54 and a removable cap 52. The device 50 comprises a dispensing end 56 near a distal end section 68 which is designed as threaded socket e.g. in order to threadedly receive a needle hub having e.g. a double-tipped injection needle in order to dispense a medicament by way of injection. As shown in FIG. 8, the housing 54 accommodates two cartridges 60 at least partially filed with a medicament. Additionally, the device 50 comprises an interface 58 to provide fluid communication between the dispensing end 56 and with any one of said cartridges 60. The interface 58 may be equipped with a fluid guiding assembly 10 as illustrated in FIGS. 1 to 5 in order to provide mixing of medicaments provided in the two cartridges 60 or to provide sequential dispensing of different medicaments via the single dispensing end 56.

As further illustrated in FIG. 8, the device comprises a display element 62 near its proximal end 66 as well as a variety of buttons or key elements 64 to control and/or to manipulate the medicament dispensing action.

The invention claimed is:

1. A fluid guiding assembly for a drug delivery device comprising:
   a first member having at least one first recess in a first surface portion,
   a second member adjacently disposed to the first member, the second member having a second surface portion facing towards the first surface portion of the first member to form an interface area between first and second members, the second member having at least one second recess in the second surface portion, wherein the at least one first recess is aligned with the at least one second recess, and
   at least one channel structure extending along the interface area of the first and second members and being formed by at least one deepening in the first member and/or in the second member,
   wherein the at least one channel structure is between the first member and the second member,
   wherein the at least one first recess is at least partially filled with a joining component comprising a material different to a material of the first and/or second member,
   wherein the joining component at least partially protrudes from the first surface portion of the first member into the at least one second recess, and
   wherein the at least one second recess is wider than the at least one first recess.

2. The fluid guiding assembly according to claim 1, wherein the second member extends at least across the deepening of the first member to form a closed fluid guiding channel structure.

3. The fluid guiding assembly according to claim 1, wherein the joining component is configured to bond the first member and the second member responsive to thermal energy applied to the joining component.

4. The fluid guiding assembly according to claim 1, wherein the at least one deepening comprises a first deepening in the first member and a second deepening in the second member, and wherein the first deepening corresponds in size and position with the second deepening.

5. The fluid guiding assembly according to claim 1, wherein the joining component is frictionally or positively engaged with the at least one second recess.

6. The fluid guiding assembly according to claim 1, wherein the joining component and the first member are injection molded by way of a two- or multi-component injection molding process.

7. The fluid guiding assembly according to claim 1, wherein the joining component has a larger absorption coefficient for a predefined spectral range of electromagnetic radiation than the material of the first and/or second members.

8. The fluid guiding assembly according to claim 7, wherein the joining component is doped with one or more radiation absorbing particles that match with the predefined spectral range.

9. The fluid guiding assembly according to claim 7, wherein the first member and the second member are substantially transparent to electromagnetic radiation in the predefined spectral range.

10. A drug delivery device adapted to dispense a predefined amount of a medicament via an outlet, comprising:
    a housing to receive at least one cartridge at least partially filled with a medicament,
    a dispensing end to dispense a predefined amount of the medicament, and
    a fluid guiding assembly according to claim 1 disposed between the cartridge and the dispensing end, wherein the at least one channel structure of the fluid guiding assembly is arranged in a fluid path between the at least one cartridge and the dispensing end.

11. The drug delivery device of claim 10, wherein the fluid guiding assembly is in a needle hub.

12. The fluid guiding assembly according to claim 1, wherein an extension of the joining component in a direction parallel to a plane normal of (i) the first surface portion of the first member and (ii) the second surface portion of the second member is larger than a sum of a depth of the at least one recess of the first member and the at least one second recess of the second member.

13. The fluid guiding assembly according to claim 12, wherein the joining component is dimensioned such that a lateral gap is formed between the joining component and the at least one second recess of the second member.

14. A method of manufacturing a fluid guiding assembly, comprising the steps of:
    providing a first member having at least one first recess in a first surface portion,
    at least partially filling the at least one first recess with a joining component at least partially protruding from the first surface portion of the first member, arranging a second member having a second surface portion adjacent to the first member such that first and second surface portions thereof face towards each other to form an interface area between the first and the second members, wherein the second member has at least one second recess in the second surface portion, wherein the at least one first recess is aligned with the at least one second recess, wherein the joining component comprises a material different to a material of the first and/or second member, wherein the joining component at least partially protrudes from the first surface portion of the first member into the second recess, wherein the at least one second recess is wider than the at least one first recess, wherein at least one channel structure extends along the interface area and is formed by at least one deepening of the first member and/or of the second member, and wherein the at least one channel structure is between the first member and the second member, and selectively providing thermal energy to the joining component to bond together first and second members.

15. The method according to claim 14, wherein the thermal energy is provided to the joining component by way of electromagnetic radiation.

16. The method according to claim 14, wherein the first and second members are pressed together during the application of thermal energy to the joining component.

17. The method according to claim 14, wherein an extension of the joining component in a direction parallel to the surface normal of first and/or second surface portions is substantially larger than the sum of the respective depths of the at least one first recess and the at least one second recess of the first and second members.

18. The method according to claim 14, wherein the at least one second recess of the second member is wider than a lateral extension of the joining component.

19. The method according to claim 14, wherein selectively providing thermal energy to the joining component melts the joining component, and wherein upon melting of the joining component, excess material of the joining component extends into and fills a lateral gap between the joining component and the at least one second recess of the second member.

20. The method according to claim 14, wherein thermal energy is provided to the joining component until first and second surfaces of first and second members mutually abut in a direct mechanical contact.

* * * * *